(12) United States Patent
Deane

(10) Patent No.: US 9,733,238 B2
(45) Date of Patent: Aug. 15, 2017

(54) MEASUREMENT CHIP, MICROFLUIDIC DEVICE AND METHOD

(75) Inventor: Steven Charles Deane, Eindhoven (GB)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 35 days.

(21) Appl. No.: 13/985,383

(22) PCT Filed: Feb. 9, 2012

(86) PCT No.: PCT/IB2012/050585
§ 371 (c)(1),
(2), (4) Date: Aug. 14, 2013

(87) PCT Pub. No.: WO2012/110922
PCT Pub. Date: Aug. 23, 2012

(65) Prior Publication Data
US 2013/0323125 A1  Dec. 5, 2013

(30) Foreign Application Priority Data

Feb. 18, 2011  (EP) .................................... 11155003

(51) Int. Cl.
*G01N 15/06* (2006.01)
*G01N 33/00* (2006.01)
(Continued)

(52) U.S. Cl.
CPC ........ *G01N 33/5094* (2013.01); *B01L 3/5027* (2013.01); *G01N 15/1056* (2013.01);
(Continued)

(58) Field of Classification Search
CPC ........ G01N 15/06; G01N 33/00; G01N 33/48; B01L 3/00
(Continued)

(56) References Cited

U.S. PATENT DOCUMENTS 6,062,261 A  5/2000 Jacobson
2003/0073089 A1  4/2003 Mauze
(Continued)

FOREIGN PATENT DOCUMENTS

CN  101487822 A  7/2009
CN  101650370 A  2/2010
(Continued)

OTHER PUBLICATIONS

Cheung K. et al., "Impedance Spectroscopy Flow Cytometry: On-Chip Label-Free Cell Differentiation", Cytometry. Part A, John Wiley, Hoboken, NJ, US, vol. 65A, Jan. 1, 2005 (Jan. 1, 2005), pp. 124-132, XP002534498.
(Continued)

*Primary Examiner* — Brian J Sines
(74) *Attorney, Agent, or Firm* — Larry Liberchuk

(57) ABSTRACT

A measurement chip (100) is disclosed for use with a microfluidic resistance network (20) comprising a microfluidic sample preparation stage (34, 38), a sample outlet (42) and a waste outlet (44) both in fluidic communication with said preparation stage. The measurement chip comprises a sample channel (104) for receiving a sample from said sample outlet (42), the sample channel comprising measurement means (120, 130) and having a first fluidic resistance; and a waste channel (114) for receiving a waste stream from said waste outlet (44) and having a second fluidic resistance.

8 Claims, 5 Drawing Sheets

Figure 1:
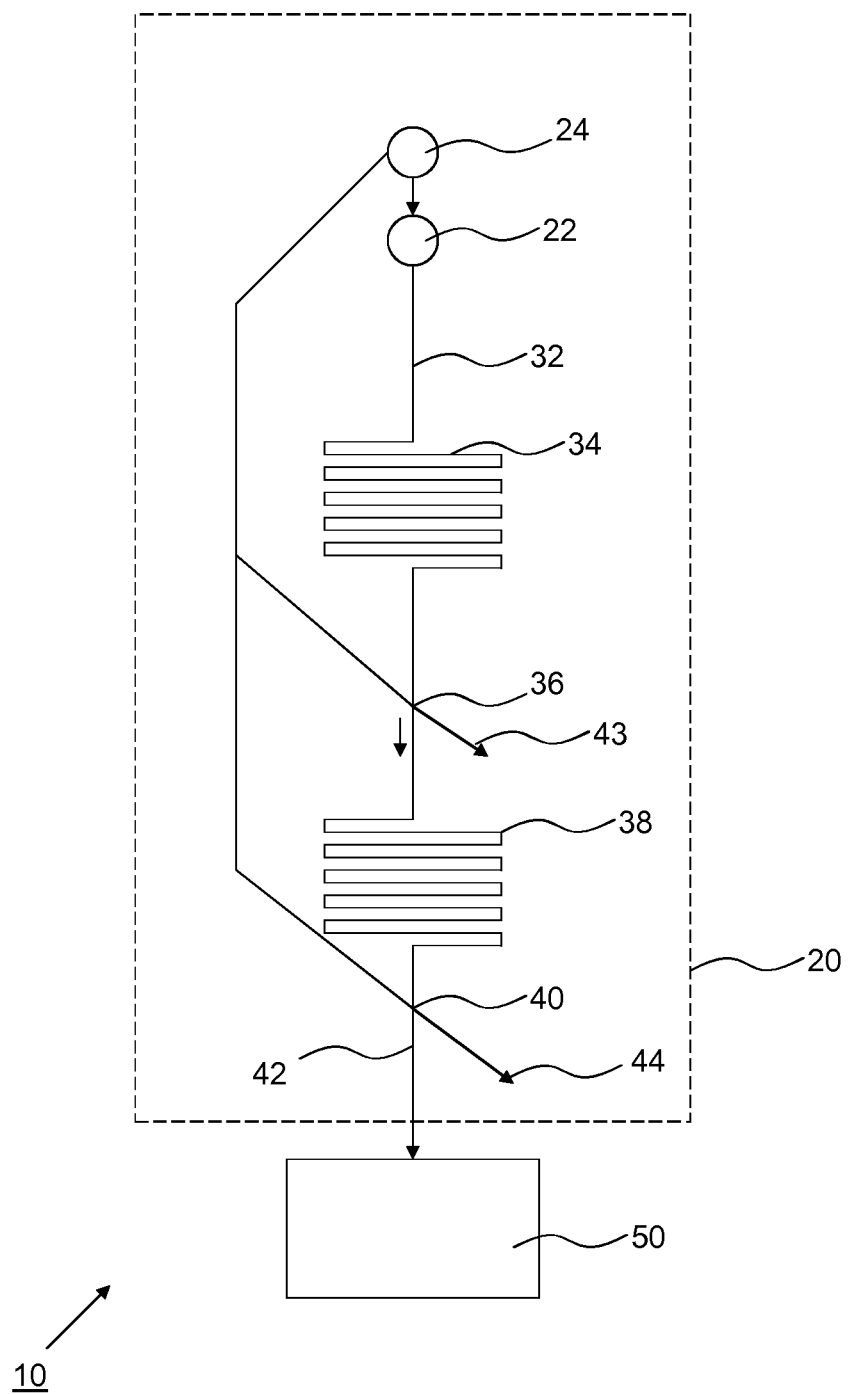

(51) Int. Cl.
*G01N 33/48* (2006.01)
*B01L 3/00* (2006.01)
*G01N 33/50* (2006.01)
*G01N 15/10* (2006.01)
*G01N 1/38* (2006.01)

(52) U.S. Cl.
CPC ... *B01L 2200/0652* (2013.01); *B01L 2200/10* (2013.01); *B01L 2300/0645* (2013.01); *B01L 2300/0816* (2013.01); *B01L 2300/0867* (2013.01); *B01L 2300/0883* (2013.01); *G01N 2001/383* (2013.01); *Y10T 29/49117* (2015.01)

(58) Field of Classification Search
USPC .......................... 422/50, 68.1, 502, 503, 504
See application file for complete search history.

(56) References Cited

U.S. PATENT DOCUMENTS

| | | |
|---|---|---|
| 2008/0003678 A1 | 1/2008 | Hattori |
| 2009/0233330 A1 | 9/2009 | Sachs |
| 2010/0159573 A1 | 6/2010 | Chung |

FOREIGN PATENT DOCUMENTS

| | | |
|---|---|---|
| EP | 2148193 A1 | 1/2010 |
| WO | WO9604547 A1 | 2/1996 |
| WO | WO9944740 A1 | 9/1999 |
| WO | WO2005114144 A1 | 12/2005 |
| WO | WO2006106643 A1 | 10/2006 |
| WO | WO2007024485 A2 | 3/2007 |
| WO | WO2007050539 A2 | 5/2007 |
| WO | WO2007084425 A2 | 7/2007 |
| WO | WO2010086786 A1 | 8/2010 |
| WO | WO2010086797 A1 | 8/2010 |

OTHER PUBLICATIONS

Van Kampen et al."Standardization of Hemoglobinometry II, The Hemiglobincyanide Method", Clinica Chimica Acta, Jan. 10, 1961, p. 538-544, Clinical Chemical Laboratory, Diakonessenhuis and Institute of Physiology, University of Groningen The Netherlands.

MEASUREMENT CHIP, MICROFLUIDIC DEVICE AND METHOD

FIELD OF THE INVENTION

The present invention relates to a measurement chip for use with a microfluidic resistance network comprising a microfluidic sample dilution stage, a sample outlet and a waste outlet both in fluidic communication with said dilution stage, the measurement chip comprising a sample channel for receiving a sample from said sample outlet, the sample channel comprising measurement means and having a first fluidic resistance.

The present invention further relates to a microfluidic device having such a measurement chip and microfluidic network.

The present invention yet further relates to a method of manufacturing such a measurement chip.

BACKGROUND OF THE INVENTION

In healthcare, there is a trend towards the development of so-called Point Of Care (POC) devices, which are small devices, often with disposable components such as cartridges, that can be used in diagnosis and treatment of patients as an alternative to large and expensive analysis equipment.

A widely used diagnostic test is a Full blood count (FBC) test, which is a diagnostic test that is used to measure cellular composition of blood. It may give information about the status of an immune system of a patient, about the ability of the blood to disseminate oxygen and/or about the ability of the blood to effectively clot. As such, it is a fundamental test that is often used as an initial "general purpose" diagnostic tool or as a more targeted monitoring solution. Examples of care cycles that include a full blood count as a monitoring tool include oncology, arthritis and Crohn's disease. As many as 300 million FBC tests are performed each year in the developed world.

Currently, large scale commercial laboratory instruments known as haematology analyzers are used to automatically perform all measurements that comprise the FBC. The high cost and complexity of these devices, coupled to the need for venous blood, means that they are mostly large scale, centralized facilities. There is a clear clinical need for performing FBC in a near patient setting, particularly for applications that require a full blood count to monitor the progression and/or treatment of a disease.

Previously, microfluidic point of care devices have been developed which are capable of measuring individual components of the FBC. In that area, Hb measuring devices, WBC counters capable of performing a white blood cell differential and platelet count devices, devices which optically count and determine size of red blood cells are available. For cell counting, current haematology analyzers typically employ electrical coulter counting and/or optical scattering methods to count and differentiate white cells and to count and determine size of the red blood cells and platelets.

At the moment only few examples of micro fluidic coulter counter technologies exist. One example combines a coulter counter with a Hb measurement. Another example of counting cells is by flow-through impedance spectroscopy. This is a flow cytometry analysis which is especially suited for a micro fluidic format. This technique is capable of differentiating between lymphocytes, monocytes and neutrophils in lysed blood, and of counting and sizing red blood cells and platelets.

The current "gold-standard" for Hb measurement is the photometric cyanmethaemoglobin (HbCN) method disclosed in Standardization of hemoglobinometry II, The hemiglobincyanide method, Clin Chim Acta, 1961, 6, p. 38-44. This method involves chemical lysis of the red blood cells and subsequent labelling of all the Hb that these cells release with a cyanide ion. The labels produce a defined absorption profile with a maximum at 540 nm. By measuring the optical absorption at 540 nm, the concentration of Hb can be determined. Furthermore, the high stability of HbCN means that it is easy to supply a calibration standard.

The most common red blood cell lysis/cyanide conversion reagent is known as Drabkin's reagent. Drabkin's reagent contains Potassium Cyanide, which is extremely toxic. This reagent only works for very large dilutions in whole blood (1:251), since red blood cell lysis relies on the low ionic strength of the reagent to induce osmotic shock. This large dilution causes an inherent imprecision in the method. Furthermore, to measure the optical absorption at 540 nm, very long optical path lengths of ~1 cm are required. Finally, in some pathological samples, turbidity can lead to erroneously high absorption readings, which in turn will give rise to an incorrect Hb concentration.

To avoid the problems associated with toxicity and turbidity, many other optical means of measuring Hb have been developed. A known point of care device uses sodium azide to convert the Hb to an azide-coordinated Hb derivative (azidemethemoglobin, HbNs). This method itself lends to short path length (0.1 mm) absorption spectroscopy, since dry reagents remove the need for dilution of the whole blood. Two absorbance readings are taken to determine the HbN3 concentration, i.e. one at the absorption maximum (565 nm) and one at 800 nm to correct for turbidity.

For the point of care WBC/Hb counter, a RBC lysis solution has been developed that preserves the WBCs while at the same time labeling the Hb molecule with imidazole. In a similar way as described above, the optical absorption of the imidazole labeled Hb species is measured at two wavelengths, i.e. one at the absorption peak and one to correct for turbidity and scattering effects for the white blood cells. The same solution may also be passed through a coulter counter to perform the cell count.

Another known lysis/Hb conversion reagent is based on sodium lauryl sulphate/sodium dodecyl sulphate (SLS/SDS). The SDS lyses all the blood cells and labels the Hb to get an SDS-coordinated derivative. Since SDS is a surfactant molecule, turbidity correction is not necessary and so a single absorption reading at 535 nm is taken to determine the Hb concentration. This method is designed for high dilutions of Hb, so the inherent imprecision present in the HbCN measurement is still present in the HbSDS one.

All the above described devices and techniques are capable of performing specific measurements from a fingerprick of blood. However, none of the above described devices and techniques are capable of measuring all parameters that are required for an FBC in a single POC measurement. Recently, a micro fluidic device capable of performing a FBC in a single POC measurement has been disclosed in WO 2010/086786. This microfluidic device comprises a two sample preparation stages, one for diluting a portion of a blood sample with a lysis agent for a white blood cell count and a quench solution and providing the diluted portion to an impedance measurement means and a second dilution stage for diluting a further portion of the blood sample with a diluent for haemoglobin measurement and providing the diluted further portion to a measurement means for determining properties of red blood cells, such as RBC count, HB count and platelet count. The diluent is fed to the blood sample several times to obtain a high dilution ratio. Consequently, only a fraction of the RBC count sample is used for the actual RBC count, with well over 90% of the various dilution stages being fed to waste.

It is of paramount importance that the flow rates through such a microfluidic device are well-defined in order to achieve accurate measurement results of the FBC. Such flow rates may be controlled using separate pumps for each fluid stream, but this is rather costly. Alternatively, the flow rates may be well-defined (i.e. tuned) at the design stage of the microfluidic device by tuning the dimensions (i.e. the fluidic resistance) of the fluid channels forming the microfluidic network. As the feature sizes of the microfluidic network are typically larger than the feature sizes of e.g. the impedance measurement chip, it is easier and therefore more cost-effective to manufacture the microfluidic network and the measurement chip in separate processes.

This, however, complicates the tuning of the microfluidic device. For instance, as only part of the diluted blood sample is fed to the measurement chip, the remainder of the diluted blood sample is typically fed to waste, as previously explained. Due to the larger feature sizes of the microfluidic network compared to the impedance measurement chip, the waste channel in the microfluidic network typically has to comprise a fluidic resistance matching element to ensure that ratio of the fluidic resistance of the waste channel and the measurement channel through the impedance measurement chip is well-defined and comparable.

It has however been found that this matching element does not always achieve satisfactory tuning. This is because the tolerances of the manufacturing process of the microfluidic network are independent of the tolerances of the manufacturing process of the impedance measurement chip, such that the required dimensions of the matching element cannot be accurately predicted.

SUMMARY OF THE INVENTION

The present invention seeks to provide a measurement chip for use with a microfluidic resistance network in which the flow rate can be more easily controlled.

The present invention further seeks to provide a microfluidic device comprising such a measurement chip.

The present invention also seeks to provide a method for manufacturing such a measurement chip.

According to an aspect of the present invention, there is provided a measurement chip for use with a microfluidic resistance network comprising a microfluidic sample preparation stage, a sample outlet and a waste outlet both in fluidic communication with said preparation stage, the measurement chip comprising a sample channel for receiving a sample from said sample outlet, the sample channel comprising measurement means and having a first fluidic resistance; and a waste channel for receiving a waste stream from said waste outlet and having a second fluidic resistance.

The present invention has been based on the realization that balancing of the flow rate of a sample from the microfluidic resistance network through the measurement chip can be much better controlled when the waste stream is also fed through the measurement chip. This is because both the sample channel and the waste channel exhibit the same reduction in feature size, and are manufactured in the same process, such that the variation in sample and waste channel dimensions becomes much smaller, thus yielding a more predictable and reproducible tuning of the flow rates through the measurement chip. This has the further advantage that the matching element in the waste line of the microfluidic resistance network may be omitted, thereby reducing the manufacturing complexity and cost of the microfluidic resistance network as the matching element typically has to be very large or very small dimensions to achieve the necessary fluidic resistance. To this end, the ratio between the first fluidic resistance and the second fluidic resistance is typically predefined to ensure the correct flow rate through the microfluidic measurement channel of the measurement chip.

In a preferred embodiment, the respective dimensions of the sample channel and the waste channel are the same. This minimizes the variability in the manufacturing tolerances of the sample channel and the waste channel. As the fluidic resistance scales with $1/d^4$, where d is the hydraulic diameter of the fluidic channel, it is important to control (variations in) the dimensions of such channels as well as possible.

In an embodiment, the measurement chip further comprises a sample inlet and a sample outlet, wherein the sample channel extends between the sample inlet and the sample outlet; and a waste inlet and a waste outlet, wherein the waste channel extends between the waste inlet and the waste outlet.

In another preferred embodiment, the sample outlet and the waste outlet are the same. It has been found that the sample channel and the waste channel may share the same outlet without affecting the respective fluidic resistances of these channels. This has the advantage that the manufacturing cost of the measurement chip can be reduced as one less outlet needs to be provided.

In yet another embodiment, the measurement chip comprises a plurality of said waste channels that preferably each have the same dimensions as the sample channel. This is for instance advantageous when the flow rate through the waste channel is tuned to be an integer multiple of the flow rate through the sample channel, such that the measurement chip may include said integer number of waste channels to implement the required flow rate in a controllable manner.

Said waste channels may extend between the same inlet and the same outlet, which has the advantage of reduced manufacturing cost.

Preferably, the measurement chip is a glass chip. Glass chips can be manufactured in a cost-effective manner and with excellent control over the dimensions of the fluid channels through the glass, e.g. the sample channel and the one or more waste channels.

The measurement means may comprise a first electrode pair including a first electrode and a first counter electrode and a second electrode pair downstream from said first electrode pair, the second electrode pair comprising a further electrode and a further counter electrode, wherein the first and further electrodes are arranged to be coupled to the same current signal and the first and further counter electrodes are arranged to be coupled to ground. Such an electrode arrangement is suitable for performing an impedance measurement such as a white blood cell count. The electrodes preferably are platinum electrodes.

The measurement chip of the present invention may be integrated into a microfluidic device that further comprises a microfluidic resistance network comprising a microfluidic sample preparation stage, a sample output and a waste output both in fluidic communication with said preparation stage, wherein the sample channel is in fluidic communication with said sample output and the waste channel is in fluidic communication with said waste output.

Such a microfluidic device exhibits improved controllability over the accuracy of the tuning of the flow rates through the device, thereby improving the accuracy of the measurement results obtained with the microfluidic device.

The microfluidic resistance network is preferably made of a polymer material as this allows for a cost-effective manufacturing of the microfluidic resistance network with good control over the dimensions of the microfluidic network.

In a preferred embodiment, the microfluidic device further comprises a first inlet for receiving a sample; a second inlet for receiving a diluent; and wherein the sample preparation stage comprises a chain of dilution stages for diluting said sample with said diluent in which a downstream dilution stage is arranged to further dilute the sample received from the previous dilution stage in said chain, wherein the first (36) of said dilution stages is in fluidic communication with the first inlet (22'); each of said dilution stages is in fluidic communication with the second inlet (24); and at least some of the dilution stages comprise a separate output (43, 44) for feeding part of the received sample to the waste channel (114).

The present invention is particularly applicable to microfluidic resistance networks in which a sample is heavily diluted by feeding a diluent from a single inlet to a plurality of dilution stages, as in such an arrangement a large portion of the sample is typically fed to waste, as in each dilution stage only a fraction of the incoming sample is combined with the diluent, with the remainder of the incoming sample being discarded.

In a preferred embodiment, the sample is a blood sample and the microfluidic resistance network further comprises a further sample preparation stage; a first further inlet in fluidic communication with the further sample preparation stage for receiving the blood sample; a second further inlet in fluidic communication with the further sample preparation stage for providing a lysis agent to the further sample preparation stage; a third further inlet in fluidic communication with the further sample preparation stage for providing a quench solution to the further sample preparation stage and a further sample outlet in fluidic communication with the further sample preparation stage.

Such a microfluidic device can for instance be used as a single device for performing a FBC, with the sample preparation stage comprising the chain of dilution stages preparing part of the blood sample for a RBC/platelet analysis and the further sample preparation stage preparing another part of the blood sample for a WBC count. To this end, the microfluidic device preferably further comprises an optical measurement cell for measuring a haemoglobin count. This optical measurement cell may be in fluidic communication with the first inlet via the sample preparation stage, the further sample preparation stage or may be fed off a separate blood sample inlet.

In accordance with another aspect of the present invention, there is provided a method of manufacturing measurement chip for use with a microfluidic resistance network comprising a microfluidic sample preparation stage, a sample outlet and a waste outlet both in fluidic communication with said dilution stage, the method comprising providing a glass substrate; forming a sample channel through said glass substrate; forming a waste channel through said glass substrate; and forming measurement means in said sample channel.

BRIEF DESCRIPTION OF THE EMBODIMENTS

Figure 2:
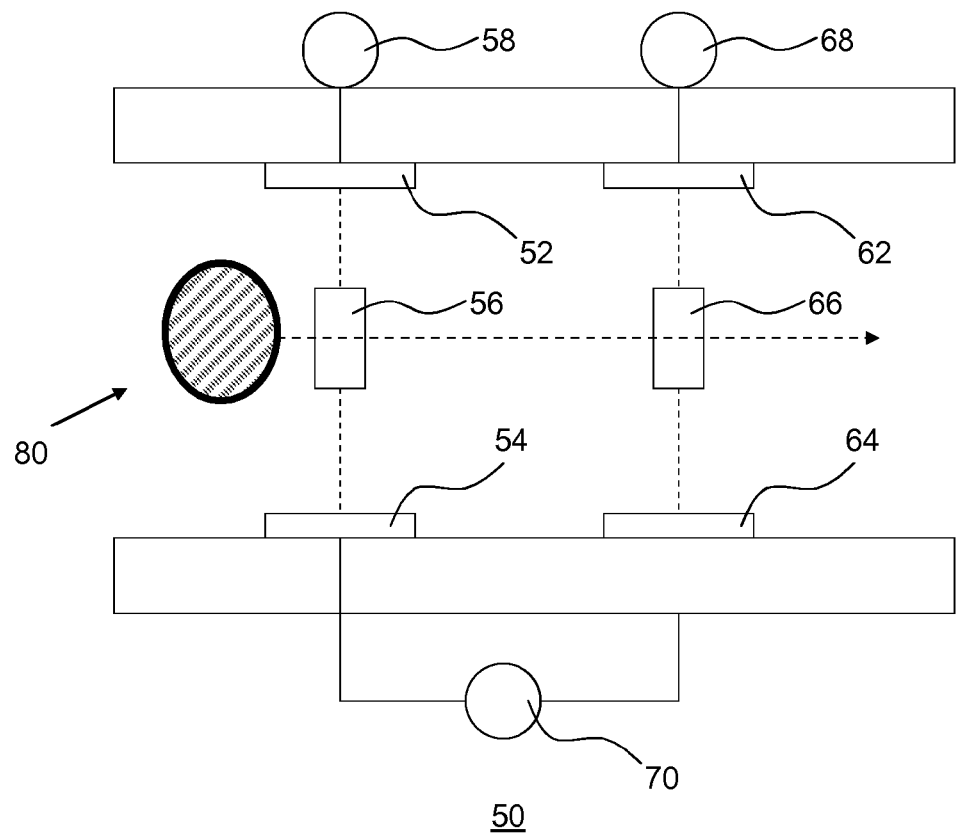
Figure 2:
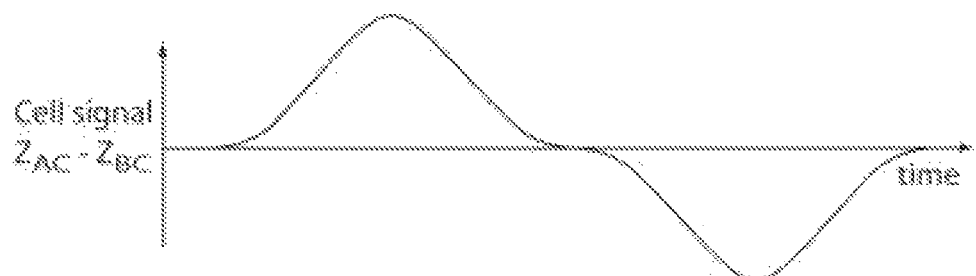
Figure 3:
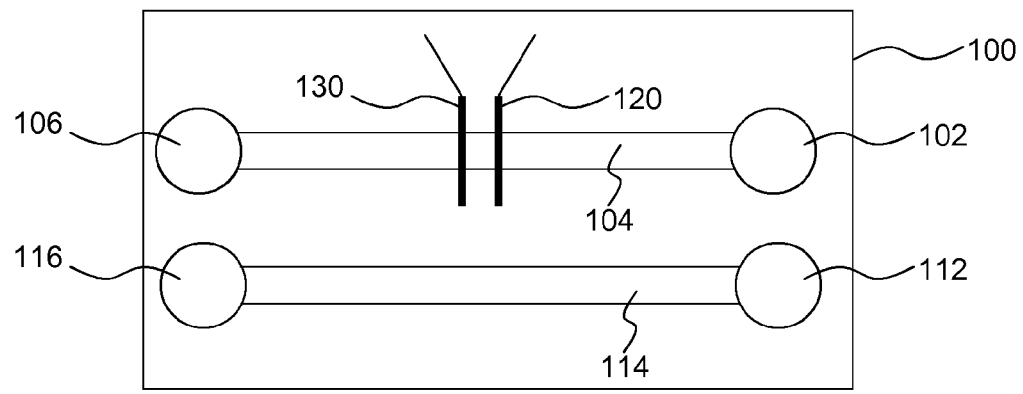
Figure 4:
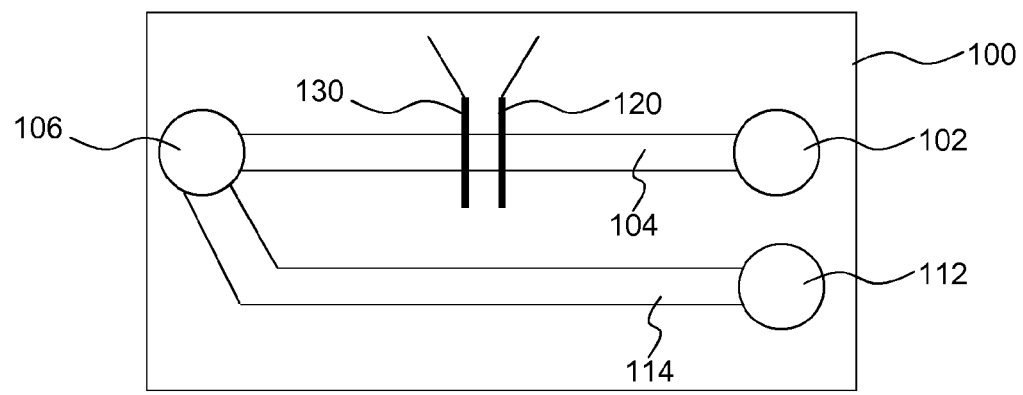
Figure 5:
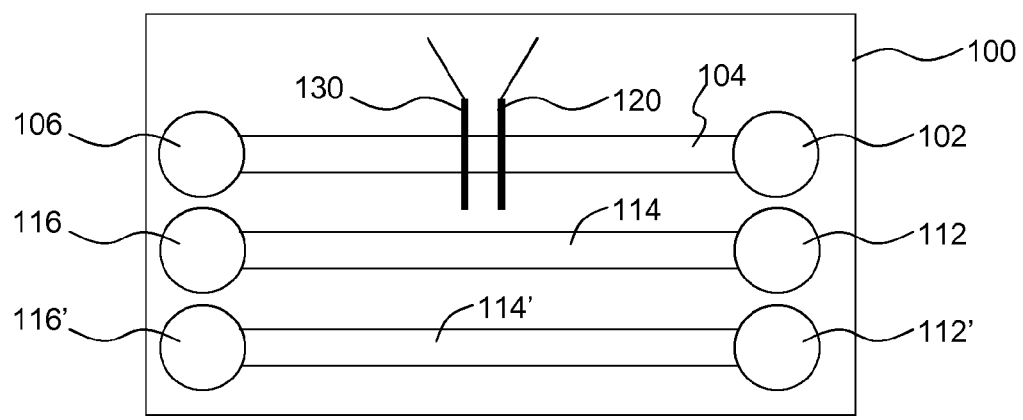
Figure 6:
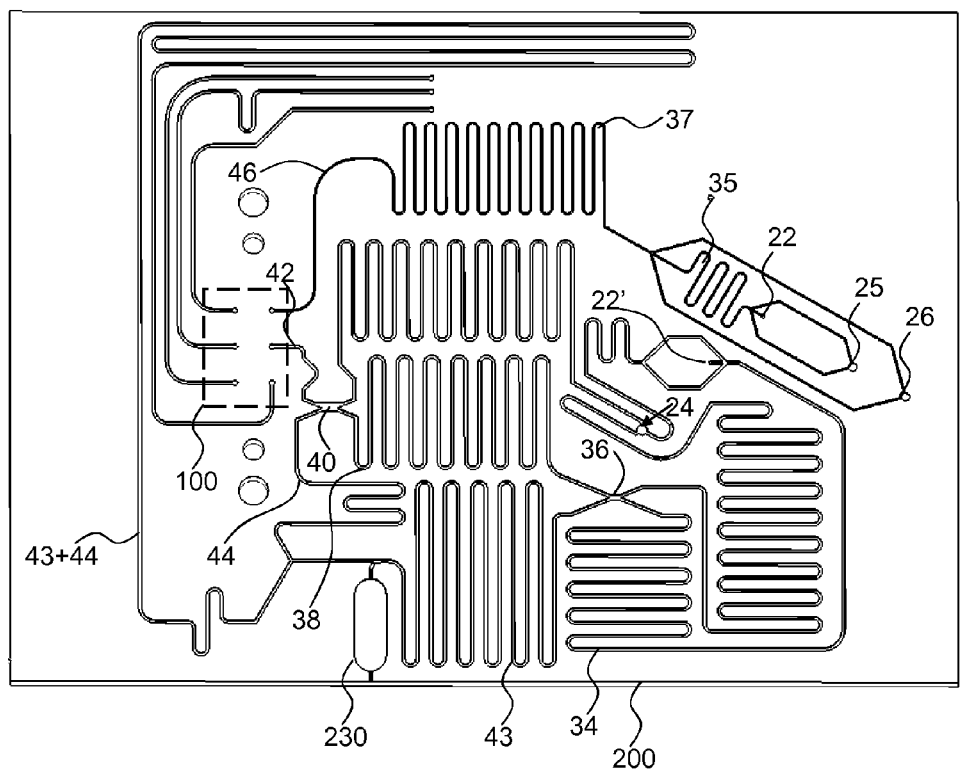
Figure 7:
Figure 8:
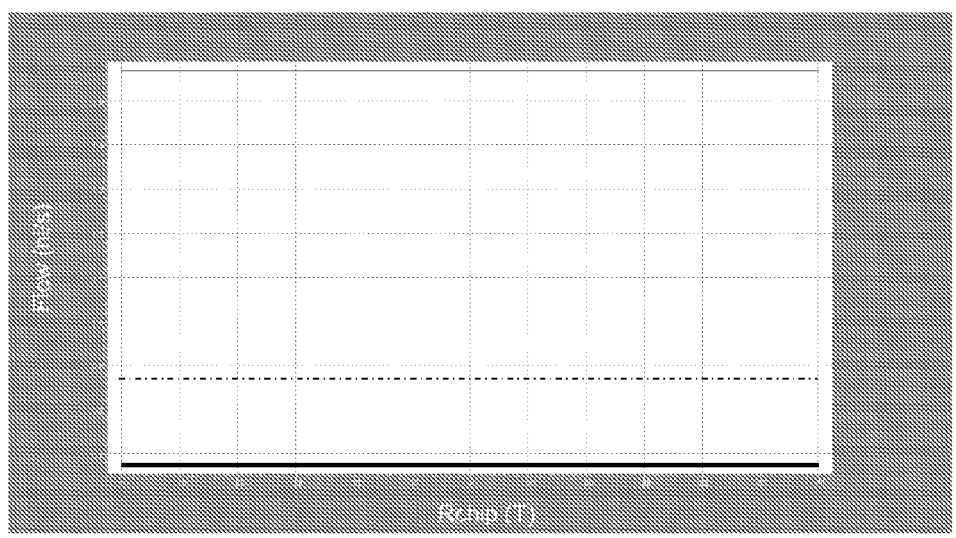

Embodiments of the invention are described in more detail and by way of non-limiting examples with reference to the accompanying drawings, wherein:

FIG. 1 schematically depicts a microfluidic device;

FIG. 2 schematically depicts an impedance measurement chip and the signal produced in such a chip;

FIG. 3 schematically depicts an embodiment of a measurement chip of the present invention;

FIG. 4 schematically depicts another embodiment of a measurement chip of the present invention;

FIG. 5 schematically depicts yet another embodiment of a measurement chip of the present invention;

FIG. 6 schematically depicts a microfluidic device according to an embodiment of the present invention;

FIG. 7 depicts the simulated variation in flow rate through key components of a microfluidic network as a function of measurement chip resistance in a prior art microfluidic device; and FIG. 8 depicts the simulated variation in flow rate through key components of a microfluidic network as a function of measurement chip resistance in a microfluidic device according to an embodiment of the present invention.

DETAILED DESCRIPTION OF THE DRAWINGS

It should be understood that the Figures are merely schematic and are not drawn to scale. It should also be understood that the same reference numerals are used throughout the Figures to indicate the same or similar parts.

The present invention relates to microfluidic devices that comprise a plurality of discrete components, in particular a microfluidic resistance network, which may be in the form of a disposable cartridge, and a measurement chip. The microfluidic resistance network has the purpose of sample preparation and presenting the prepared sample to the measurement chip. In the context of the present invention, the term 'microfluidic' is to relate to the behavior, precise control and manipulation of fluids that are geometrically constrained to a small, typically sub-milliliter, scale volumes, e.g. µl, nl, pl, fl volumes.

FIG. 1 schematically depicts a non-limiting example of such a microfluidic device 10, which includes a disposable microfluidic resistance network 20 and a measurement chip 50. The microfluidic resistance network 20 is designed to receive a sample such as a RBC sample at sample inlet 22. The microfluidic resistance network 20 further comprises a diluent inlet 24 for receiving a diluent, which is branched off in three different branches. A first branch is mixed with the sample at the sample inlet 22 and subsequently fed to a sample mixing or dilution stage 34, e.g. a snake stage, whereas a second branch is used to further dilute the sample at junction 36. The junction 36 is typically shaped in a particular manner to obtain a desired dilution ratio of the sample with the diluent, as for instance is explained in more detail in WO 2010/086786. A sample dilution stage 38, e.g. a microfluidic snake stage, is designed such that that the sample is in contact with the diluent for a predetermined period of time, e.g. a period of time necessary to complete the dilution of the sample and to provide the required fluidic resistance At junction 36, a substantial part of the diluted sample received from dilution stage 34 is fed to a waste channel 43, whereas a (small) fraction of the diluted sample is mixed with the diluent from the second branch of the diluent inlet 24 and fed to the sample dilution stage 38. At junction 40, the sample diluted in sample dilution stage 38 is again split in a portion fed to waste channel 44, with the remaining portion further diluted by the diluent received from the third branch of the diluent inlet 24 and subsequently fed via measurement channel 42 to the measurement chip 50. A snake stage (not shown) may be present between the junction 40 and the measurement chip 50 for the aforementioned reasons. Junction 40 is typically shaped in a particular manner to obtain a desired dilution ratio of the diluted sample received from the sample dilution stage 34 with the diluent. Suitable embodiments of diluent have for instance been disclosed in WO 2010/086786.

The microfluidic device 10 shown in FIG. 1 is particularly suited for the treatment and subsequent analysis of a FBC sample. However, it will be understood by the skilled person that design of the microfluidic resistance network 20 may be altered to prepare different types of samples, e.g. urine or saliva samples, as well as samples for non-medical evaluation, e.g. environmental samples, food samples and so on.

FIG. 2 shows the impedance measurement chip 50 in more detail. A detailed description of such an impedance measurement arrangement can be found in "Impedance spectroscopy flow cytometry: on-chip label-free cell differentiation", Cheung, K., S. Gawad, and P. Renaud, Cytometry A, 2005. 65(2): p. 124-132. FIG. 2 shows a side view of the microfluidic channel through the chip 50 and a sample cell 80 passing between the excitation electrodes 52, 62 and the detection electrodes 54, 64. The excitation electrode 52 and the detection electrode 54 form a first electrode pair and the excitation electrode 62 and the detection electrode 64 form a second electrode pair.

The excitation electrodes 52 and 62 are respectively connected to a current input signal source 58 and 68, e.g. an AC or DC input signal source. An AC input signal source is preferred as it prevents electrolysis at the electrodes. In an embodiment, the excitation electrodes 52 and 62 may share the same AC input signal source (i.e. 58=68). The detection electrodes are typically connected to a differential potential detection circuit 70, which preferably keeps the detection electrodes at an approximate ground potential. The currents passing through the fluid between the first and second electrode pair are amplified and its difference is determined in any suitable manner, e.g. using well-known analog electronics. The in-phase and out-of-phase parts of the resulting AC signal are measured using standard Lock-in-technology. Without a particle passing the electrodes the measured signal is ideally zero, although in practice always an offset is present due chip asymmetry, and potentially electronic component inaccuracies. If a particle coming from the left first passes the first electrode pair, a positive almost Gaussian shape signal is produced, as the second electrode pair acts as the reference electrode for the first electrode pair. When the particle subsequently passes the second electrode pair, a negative Gaussian shape signal is produced as the first electrode pair acts as the reference electrode for the second electrode pair. The resulting antisymmetric double Gaussian signal shape is also shown in FIG. 2. The Cell Signal may be the output of a Lock-In Amplifier measuring the current difference between both electrode pairs. In this way impedance spectroscopy can be performed for different cells, e.g. RBC or WBC.

In order to accurately determine the cell count of the sample fed through the measurement chip 50, the flow rate of the sample through the measurement chip 50 must be well defined, as the number of counted cells must be related to a well-defined sample volume. This sample volume is set by junction 40 of the microfluidic resistance network 20, and is influenced by the respective fluidic resistances of the microfluidic path through the measurement chip 50 and the microfluidic waste channel 44. In order to correctly design the junction 40, these fluidic resistances must be known at the design stage. As the hydraulic diameter of the microfluidic channel through the measurement chip 50 are typically much smaller than the hydraulic diameter of the microfluidic waste channel 44, the microfluidic waste channel 44 typically comprises a matching element (not shown) to match the fluidic resistance of the microfluidic waste channel 44 with that of the microfluidic channel through the measurement chip 50. The hydraulic diameter is the effective diameter used to approximate the behaviour of a non-circular channel, such as a square or rectangular channel.

However, as the measurement chip 50 is manufactured in a different manufacturing process than the microfluidic resistance network 20, the manufacturing process of the measurement chip 50 is typically subjected to different tolerances than the manufacturing process of the microfluidic resistance network 20. As previously mentioned, the resolution of the microfluidic resistance network 20 is typically chosen to be lower than the resolution of the measurement chip 50. For this reason, the (disposable) microfluidic resistance network 20 can be cheaply manufactured in polymer materials, e.g. plastics, whereas for the measurement chip 50 glass substrates are preferred as glass is a relatively cheap material suitable for achieving the required resolution.

The consequence of the use of these different manufacturing processes and different materials for the microfluidic resistance network 20 and the measurement chip 50 is that the tolerances in these processes and materials can lead to an unacceptably large deviation of the junction 40 from its intended performance, e.g. the volume of the sample separated from the waste stream is inaccurate. This is typically caused by independent variations in the dimensions of the microfluidic waste channel 44 and the microfluidic channel through the measurement chip 50.

FIG. 3 shows a measurement chip 100 in accordance with an embodiment of the present invention in which this problem has been overcome. In addition to the microfluidic measurement channel 104 extending between inlet 102 and outlet 106, the measurement chip 100 further comprises a microfluidic waste channel 114 extending between inlet 112 and outlet 116 for receiving the remainder of the sample from microfluidic waste channel 44. The microfluidic measurement channel 104 may comprise any suitable measurement means, e.g. an electrode arrangement such as the impedance measuring first electrode pair 120 and a second electrode pair 130 as previously explained with the aid of FIG. 2, or optical detection means, e.g. a spectrophotometer, photodiode and so on.

Any suitable electrode material may be chosen. Preferably, the electrodes are platinum electrodes although alternative electrode materials such as for example Indium Tin Oxide (ITO), titanium nitride and chromium nitride are also feasible. It should further be understood that the electrode arrangement shown in FIG. 2 has been shown by way of non-limiting example only, and that other electrode arrangements are equally feasible, such as a single pair of electrodes or a long sequence of electrode pairs as disclosed in WO2010/086797 A1. The electrode may be controlled by any suitable control signal, e.g. an AC signal as previously explained as well as a DC signal.

As the hydraulic diameter of the microfluidic waste channel 114 is much smaller than the hydraulic diameter of the microfluidic waste channel 44, the fluidic resistance of the combined waste line is entirely dominated by the fluidic resistance of the microfluidic waste channel 114, such that tolerances in the manufacturing process of the microfluidic resistance network 20 no longer affect the sample separation ratio at junction 40. This sample separation ratio is now dominated by the fluidic resistances of the microfluidic measurement channel 104 and the microfluidic waste channel 114 respectively. As the microfluidic measurement channel 104 and the microfluidic waste channel 114 are formed in the same manufacturing process, the tolerances in the dimensions of the microfluidic measurement channel 104 and the microfluidic waste channel 114 can be much better controlled, such that the volume of the sample directed towards the microfluidic measurement channel 104 at junction 40 becomes invariant of the manufacturing tolerances of both the microfluidic resistance network 20 and the measurement chip 100.

At this point, it is noted that although extending the measurement chip 100 with the microfluidic waste channel 114 increases the cost of the measurement chip 100, the overall cost of a microfluidic device including a microfluidic resistance network 20 and the measurement chip 100 is reduced as the number of incorrectly tuned devices as caused by overly large variations in manufacturing tolerances is significantly reduced.

The cost of the measurement chip 100 may be reduced by combination of the outlets of the measurement channel 104 and the microfluidic waste channel 114 as shown in FIG. 4. In FIG. 4, outlet 116 has been removed from the design of the measurement chip 100. It has been found that the combination of multiple microfluidic channels on a single outlet does not influence the respective microfluidic resistances of the multiple microfluidic channels.

Preferably, the microfluidic measurement channel 104 and the microfluidic waste channel 114 have the same dimensions, as the fluidic resistance R of a microfluidic channel scales as follows: $R \sim 1/d^4$, in which d is the hydraulic diameter of the microfluidic channel. It has been found that for microfluidic channels having different dimensions, i.e. different hydraulic diameters, different variations in the tolerances of these channels can occur, which makes it more difficult to tune the microfluidic device and in particular the microfluidic resistance network 20 including junction 40.

If nevertheless the microfluidic measurement channel 104 requires a different fluidic resistance than the microfluidic waste channel 114, this preferably is achieved by providing a plurality of microfluidic channels for the channel requiring the lower resistance. Each of the microfluidic channels in said plurality preferably have the same hydraulic diameter for the reasons already explained above. A non-limiting example of such an arrangement is shown in FIG. 5, in which in addition to the first microfluidic waste channel 114, a second microfluidic waste channel 114' between inlet 112' and outlet 116' is provided, with the waste stream from microfluidic waste channel 44 being equally divided over the first microfluidic waste channel 114 and the second microfluidic waste channel 114'.

It will be understood that many variations are possible to the measurement chip 100 shown in FIG. 5. In FIG. 5, two microfluidic waste channels 114 and 114' are shown by way of non-limiting example only. A different number of microfluidic waste channels is equally feasible; typically the measurement chip 100 comprises N microfluidic waste channels, with N being a positive integer if the ratio between the microfluidic resistance of the microfluidic measurement channel 104 and the microfluidic resistance of the microfluidic waste channels equals N ($R_{104}/R_{114, 114'}$=N). Although the two microfluidic waste channels 114 and 114' are shown to have separate inlets and outlets, it will be understood that the microfluidic waste channels 114 and 114' may share their inlets and/or outlets, or may share their outlets with the microfluidic measurement channel 104. It will further be understood that instead of or in addition to having a plurality of microfluidic waste channels, the measurement chip 100, microfluidic measurement channel 104 may also comprise one or more dummy channels preferably having the same dimensions as the microfluidic measurement channel 104 to lower the fluidic resistance of the microfluidic measurement channel 104. The measurement chip 100 may for instance comprise a microfluidic measurement channel 104 and M-1 dummy channels (not shown) as well as N microfluidic waste channels in case the desired ratio of the respective fluidic resistances is M/N. In addition, the measurement chip 100 may comprise a plurality of different measurement channels for measuring different samples or different portions of the same sample, e.g. different portions treated with different reagents to measure different aspects of the same sample, e.g. separate channels for performing a RBC and a WBC count.

The measurement chip 100 may be manufactured in any suitable manner, for instance by providing a top plate and a bottom plate, preferably glass plates, forming a pair of trenches in each of the top plate and the bottom plate, e.g. by etching or drilling such as laser drilling, forming measurement means in one of said trenches in the top plate and in the corresponding trench in the bottom plate, and placing the top plate onto the bottom plate such that a first pair of trenches combine to form the microfluidic measurement channel 104 including the measurement means and a second pair of trenches combine to form the microfluidic waste channel 114. Alternative manufacturing methods will be apparent to the skilled person, e.g. by providing a substrate, preferably glass, drilling the microfluidic measurement channel 104 and the microfluidic waste channel 114 in the substrate, e.g. by laser drilling and forming the measurement means in the microfluidic measurement channel 104.

FIG. 6 schematically depicts an embodiment of a microfluidic device 200 of the present invention. The microfluidic device 200 is designed to perform a FBC on a single blood sample. To this end, the microfluidic device 200 comprises a first blood sample input 22 into a lysis stage for lysing red blood cells, including an inlet 25 for receiving a RBC lysing agent such as a formic acid/saponin mixture, and an inlet 26 for receiving a quenching agent for quenching the lysed sample to protect the white blood cells from lysing. A non-limiting example of a suitable quenching agent is a NaCl/NaHCO3 solution. The lysing stage may comprise any suitable number of snake stages. Two snake stages 35 and 37 are shown by way of non-limiting example. The outlet channel 46 of the lysing stage is fed into the measurement chip 100 of the present invention. As the entire sample is fed through the measurement chip 100, there is no separate waste channel through the chip 100 for the lysis stage.

The microfluidic device 200 further comprises a second blood sample inlet 22', which is fed into a red blood cell/platelet treatment stage. The first blood sample inlet 22 and the second blood sample inlet 22' may be separate branches of a single blood sample inlet (not shown) or may be independently fed with separate blood samples, e.g. separate portions of the same blood sample. The blood cell/platelet treatment stage further comprises a diluent sample inlet 24, which is split in three branches. A first branch is fed to the blood sample inlet 22' where the incoming blood sample is diluted by a predefined ratio, e.g. 20:1, and the second and third branch are fed to junctions 36 and 40 respectively, where the diluent is mixed with blood sample. Consequently, large dilution ratios can be achieved with only a small amount of diluent as no diluent is wasted in the microfluidic device 200.

Each of the junctions 36 and 40 has a first output for generating a waste stream essentially comprising of a large fraction of the incoming sample only, and a second output for generating a mixture of the small fraction of the incoming sample with all of the incoming diluent. The various fluidic channels may contain one or more snake stages, e.g. stages 34 and 38, which may be included to tune the mixing ratio and the fluidic resistance of the fluidic channel, as is known per se. The sample output 42 of the junction 40 is fed to the sample channel of the measurement chip 100, e.g. the measurement channel 104 as for example shown in FIG. 3 for measuring a red blood cell count, whereas the waste output 44 the junction 40 is fed to the waste channel of the measurement chip 100, e.g. the waste channel 114 as for example shown in FIG. 3, for reasons previously explained. In an embodiment, the waste streams of the respective dilution stages, i.e. junctions 36, 40 may be combined prior to feeding the waste through the waste channel 114 of the measurement chip 100. This is shown in FIG. 6 as the microfluidic branch labelled 43+44.

Compared to the microfluidic resistance network 20 in the microfluidic device 10, the microfluidic resistance network 20 of the microfluidic device 200 can be simplified by the omission of the matching element in the (combined) microfluidic waste channel (43+) 44, as this resistance matching is now achieved by feeding the waste through the higher resolution (i.e. smaller dimensioned) microfluidic waste channel 114.

In FIG. 6, the waste channel 43 from the first junction 36 is branched off towards to a Hb sample chamber 230 including an optical measurement cell for preparing the unused portion of the blood sample for a Hb absorption measurement in the optical measurement cell in the Hb sample chamber 230. The Hb sample chamber may contain some reagents in dry form that lyse and label the blood sample to perform the Hb measurement. In this arrangement, only a small sample of blood needs to be labeled for the Hb absorption measurement, which is advantageous as the labeling reagents can be toxic, e.g. comprise cyanide, as necessarily they must bind to Hb.

It is pointed out that FIG. 6 shows a non-limiting example of a microfluidic device 200 of the present invention. The microfluidic device 200 may for instance be a microfluidic device as described in detail in WO2010/086786. In FIG. 6, a part of the sample is branched off the RBC count preparation stage for Hb measurement preparation in the preparation stage 230. It will be understood that it is equally feasible to branch off part of the sample from the WBC count preparation stage for Hb sample preparation instead. The microfluidic device 200 may alternatively be arranged to generate three separate branches from the blood sample inlet 22, i.e. one branch for RBC/platelet count sample preparation, one branch for WBC sample preparation and one branch for Hb measurement sample preparation. Other variations will be apparent to the skilled person.

It will further be understood that the present invention is not limited to microfluidic devices for FBC measurements. The present invention may be applied to any microfluidic device in which a tuned microfluidic resistance network 20 is manufactured separate from a measurement chip 100, and in which only a fraction of the sample prepared in the tuned microfluidic resistance network 20 is to be fed to the measurement chip 100, e.g. microfluidic devices for analysis of bodily fluids such as saliva and urine, microfluidic devices for analysis of environmental samples, food samples and so on.

FIG. 7 depicts the result of a simulation of the flow rates through key components of the tuned microfluidic resistance network 20 in the microfluidic device 10 of FIG. 1 as a function of the fluidic resistance of the microfluidic measurement channel of the measurement chip 50. In FIG. 7, the thin solid line is the flow rate from junction 40 to the waste outlet 44, the thick solid line is the flow rate of the sample into junction 40, the dashed line (---) is the flow rate from junction 40 towards the sample outlet 42 and the chain line (-•-•) is the flow rate of the diluent into the junction 40. As the waste stream from junction 40 is not fed through the measurement chip, these flow rates are affected by a change in the fluidic resistance of the microfluidic measurement channel of the measurement chip 50. Importantly, as the flow rates change, the dilution ratios change as well such that the absolute cell counts per unit of the sample are no longer (accurately) known. It will be apparent that such variations in flow rate are unacceptable.

FIG. 8 depicts the result of a simulation of these flow rates through the tuned microfluidic resistance network 20 in the microfluidic device 200 of FIG. 6 as a function of the fluidic resistance of the microfluidic measurement channel 104 of the measurement chip 100. As the waste stream from junction 40 is fed through the microfluidic waste channel 114 of the measurement chip 100, these flow rate are no longer dependent of changes in the fluidic resistance of the microfluidic measurement channel 104 of the measurement chip 100, due to the fact that the fluidic resistance of the microfluidic waste channel 114 varies in the same manner. This clearly demonstrates that the provision of the waste channel on the measurement chip 100 significantly improves the robustness of the overall microfluidic device 200 against variations (tolerances) in the manufacturing process of its components.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. The invention can be implemented by means of hardware comprising several distinct elements. In the device claim enumerating several means, several of these means can be embodied by one and the same item of hardware. The mere fact that certain measures are recited in mutually different dependent claims does not indicate that a combination of these measures cannot be used to advantage.

The invention claimed is:

1. A measurement chip for use with a microfluidic resistance network for measuring parameters in a full blood count test, the measurement chip comprising:
   a sample channel for providing a flow of a sample stream in one direction only from a sample inlet to a sample outlet, the sample inlet receiving the sample stream from the microfluidic resistance network, the sample channel having a first fluidic resistance; and
   a waste channel for providing a flow of a waste stream in one direction only from a waste inlet to a waste outlet, the waste inlet receiving the waste stream from the microfluidic resistance network, the waste channel having a second fluidic resistance, wherein a ratio between the first fluidic resistance and the second fluidic resistance is predetermined.

2. The measurement chip of claim 1, wherein the respective dimensions of the sample channel and the waste channel are the same.

3. The measurement chip of claim 2, wherein the sample outlet and the waste outlet are the same.

4. The measurement chip of claim 1, wherein the chip comprises a plurality of said waste channels.

5. The measurement chip of claim 4, wherein said waste channels share the same waste inlet and/or the same waste outlet.

6. The measurement chip of claim 1, wherein the chip is a glass chip.

7. The measurement chip of claim 1, further comprising a first electrode pair including a first electrode and a first counter electrode, the measurement chip further comprising a second electrode pair downstream from said first electrode pair, the second electrode pair comprising a second electrode and a second counter electrode, wherein the first and second electrodes are configured to be coupled to the same current signal, and the first and second counter electrodes are configured to be coupled to ground.

8. The measurement chip of claim 7, wherein said electrodes and counter electrodes are platinum electrodes.

* * * * *